United States Patent [19]

Bartholmes et al.

[11] Patent Number: 5,578,204
[45] Date of Patent: Nov. 26, 1996

[54] APPARATUS FOR RECOVERY AND BUFFER EXCHANGE AND/OR CONCENTRATION OF DISSOLVED MACROMOLECULES FROM A MIXTURE OF MACROMOLECULES

[76] Inventors: Peter Bartholmes, Meesmannstrasse 82, D-58456 Witten; Michael Kaufmann, Flaspoete 69, D-44388 Dortmund; Thomas R. Schwarz, Ginsterweg 6, D-42799 Leichlingen, all of Germany

[21] Appl. No.: 416,902

[22] PCT Filed: Oct. 13, 1993

[86] PCT No.: PCT/EP93/02827

§ 371 Date: Jun. 6, 1995

§ 102(e) Date: Jun. 6, 1995

[87] PCT Pub. No.: WO94/08684

PCT Pub. Date: Apr. 28, 1994

[30] Foreign Application Priority Data

Oct. 15, 1992 [DE] Germany .................. 42 34 728.9

[51] Int. Cl.⁶ .................................................. B01D 15/08
[52] U.S. Cl. .................. 210/198.2; 210/321.89; 210/500.23; 210/656
[58] Field of Search .................. 210/635, 656, 210/659, 198.2, 321.88, 321.89, 321.9, 500.23; 422/70

[56] References Cited

U.S. PATENT DOCUMENTS

| 4,195,073 | 3/1980 | Newman | 424/1 |
|---|---|---|---|
| 4,448,691 | 5/1984 | Davis | 210/656 |
| 4,451,374 | 5/1984 | Peterson | 210/656 |
| 4,474,664 | 10/1984 | Stevens | 210/656 |
| 4,529,521 | 7/1985 | Cortes | 210/656 |
| 4,732,686 | 3/1988 | Small | 210/656 |
| 4,751,004 | 6/1988 | Stevens | 210/659 |
| 4,794,088 | 12/1988 | Miyaki et al. | 210/199.2 |
| 4,836,928 | 6/1989 | Aoyagi | 210/656 |
| 4,957,620 | 9/1990 | Cussler | 210/656 |
| 5,160,625 | 11/1992 | Jonsson | 210/656 |
| 5,160,627 | 11/1992 | Cussler | 210/656 |
| 5,279,972 | 1/1994 | Heckberg | 210/656 |

FOREIGN PATENT DOCUMENTS

| 0058168 | 5/1987 | European Pat. Off. | 210/198.2 |
|---|---|---|---|
| 0348508 | 1/1990 | European Pat. Off. | 210/198.2 |
| 2724918 | 12/1978 | Germany | 210/198.2 |

OTHER PUBLICATIONS

English Abstract of Japan Patent 50160474 Dec. 1975.

Primary Examiner—Ernest G. Therkorn
Attorney, Agent, or Firm—Collard & Roe, P.C.

[57] ABSTRACT

The invention relates to an apparatus for recovery and buffer exchange and/or concentration of dissolved macromolecules from a mixture of macromolecules. The apparatus includes a liquid chromatography unit and at least one hollow fiber membrane cartridge connected downstream of the liquid chromatography unit.

3 Claims, 1 Drawing Sheet

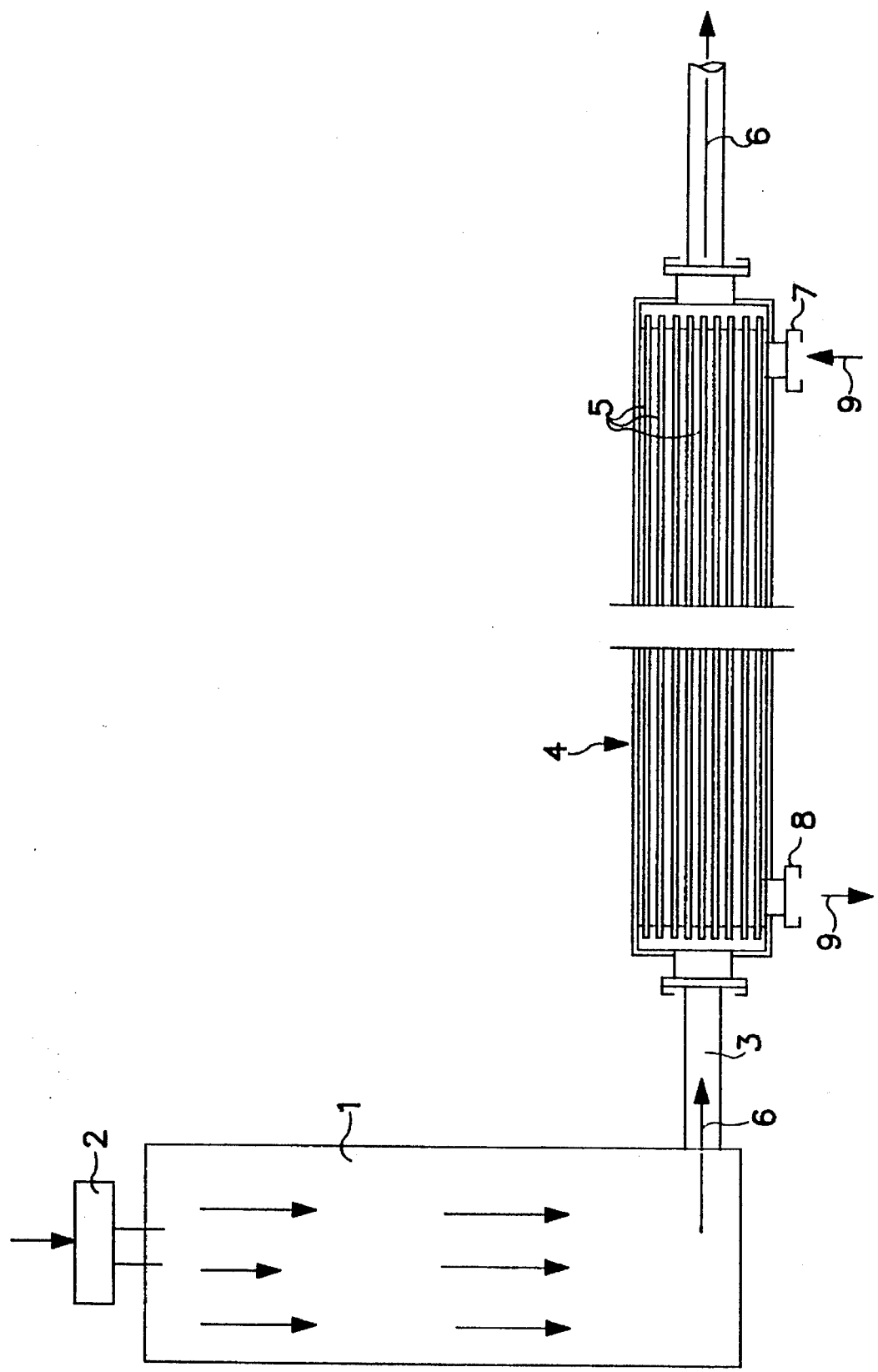

APPARATUS FOR RECOVERY AND BUFFER EXCHANGE AND/OR CONCENTRATION OF DISSOLVED MACROMOLECULES FROM A MIXTURE OF MACROMOLECULES

The invention relates to an apparatus for recovery and buffer exchange and/or concentration of dissolved macromolecules from a mixture of macromolecules, comprising a liquid chromatography unit and at least one hollow fibre membrane cartridge provided in the outlet tubing of the liquid chromatography unit.

Among the standard biochemical techniques there are various chromatographic methods, in which differences in mass, form, affinity, charge or polarity of the molecules are utilized for their separation. In ion exchange, gel filtration and affinity chromatography, liquid chromatography units are used to separate mixtures of macromolecules in their individual constituents.

Besides the individual constituents of a mixture of macromolecules the eluate of a liquid chromatography column contains low-molecular substances, e.g. salts, which were used to compensate for the interactions between the macromolecules and the stationary phase of the chromatography column. After the chromatography, these substances must be removed from the eluate for they are to interfere, e.g. in subsequent steps of detection or further treatment, and are for this reason undesired in the preparations.

In preparative biochemistry so-called "discontinuous equilibrium dialysis" is applied to eliminate low molecular weight components from the eluate of the liquid chromatography unit as well as to exchange the buffer solution containing the mixture of macromolecules. In this method the eluate containing the various molecular species is filled in a dialysis tube, which both ends are closed by clamps. The wall of the dialysis tube consist of a semipermeable membrane, which allows low-molecular substances, e.g. water or salts, to pass while macromolecules are retained. In this way electrolytes or other low molecular weight substances contained in the eluate can diffuse through the membrane until osmotic equilibrium is attained. The dialysis tube filled with eluate is immersed in a vessel containing a large amount of water or buffer solution for several hours. By changing the outer liquid frequently enough, the low molecular weight components can be completely extracted and/or the buffer solution can be exchanged.

When macromolecules are separated according to size by means of gel filtration, the contamination of the preparation with undesired low-molecular compounds is no longer the main problem; it is rather the high dilution of the macromolecules during the elution from the chromatography column which gives reason for concern. This problem is encountered frequently in other chromatographic separation methods as well. Concentrated solutions of high molecular weight substances (for example polyethylene glycol) are used as dialysis fluid to concentrate the eluate, as they show a high affinity for water and thus extract water from the macromolecule solution, but cannot diffuse through the dialysis membrane.

The described procedure is troublesome and requires a considerable amount of time and outlay for equipment. In particular, if the eluate is divided among a large number of individual containers (fractionation) to separate the individual macromolecular species, the method becomes almost unfeasible. Delays, unavoidable when using this method, are particularly disadvantageous, when the sensitive macromolecules remain for too long in an unsuitable buffer solution. This problem appears frequently in the case of enzymatic preparations: the enzyme is often so labile that the troublesome steps of exchanging buffer and/or concentrating by dialysis lead to a considerable loss of enzymatic activity in the preparation.

In the EP-B1-00 58 168, an apparatus has been described, wherein a hollow fibre membrane reactor is used in connection with a liquid chromatography unit. In this hollow fibre membrane reactor the eluate of the liquid chromatography unit is treated with reagents, which react with constituent groups of the samples and/or the eluent to provide a better and faster analysis.

This apparatus is not suited for recovery of biochemical preparations. In particular, when preparations containing labile macromolecules are recovered, this apparatus seems to be problematic, since the macromolecules muse remain in the buffer solution during the time needed for the complete withdrawal of the low-molecular constituents from the eluate. This could lead to a considerable loss of activity in the preparation. Furthermore, due to a too long dwell time of the macromolecules in the reactor, the macromolecules separated by liquid chromatography can diffuse in the buffer solution. This represents a considerable disadvantage, when macromolecules are preparatively extracted and especially, when they are separated for analytical purposes.

Furthermore, a method and an apparatus which allow the analysis of a sample containing constituents of low and intermediate molecular weight and the separation of these constituents by means of liquid chromatography are described in U.S. Pat. No. 4,794 088. The hollow fibre membrane disclosed herein is an ion exchange membrane, especially permeable for electrolytes. However, its permeability for non-electrolyte compounds (e.g. low-molecular carbohydrates as saccharose) is very low. For this reason the membrane is not suitable for the exchange of buffer solutions containing such compounds. Neither hollow fibre membrane cartridges as used for dialysis in artificial kidney are suitable for buffer exchange and/or concentration of the eluate of a liquid chromatography unit containing the separated macromolecules in a particular sequence. Such hollow fibre membrane cartridges contain a large number (up to 8,000) comparatively short (200 to 300 mm) hollow fibres. The ratio of the number of hollow fibres to the length of the hollow fibres is here between 27 and 40 $mm^{-1}$ The aim is to provide a surface as large as possible for diffusion in the dialysis fluid of the low-molecular substances (metabolic products as urea, uric acid, ions inter alia) contained in blood, as to provide an equal distribution of blood among the many hollow fibres. As a consequence of using such a cartridge for recovery and buffer exchange and/or concentration of an eluate of a liquid chromatography unit, macromolecules separated by means of liquid chromatography would be uniformly distributed among the many hollow fibres and the achieved separation would be revoked partially or completely. The use of a such hollow fibre membrane cartridge for the purpose of the invention would be in principle disadvantageous.

It is the object of the invention to further develop the apparatus of prior art to shorten the dwell time of the macromolecular species in the buffer solution, as to enable buffer exchange and/or concentration of the buffer solution to be carried out continuously, as well as to reduce the outlay for equipment without removing totally or partially the separation of macromolecules achieved by means of liquid chromatography.

According to the invention the object is achieved in conjunction with the prior art by a hollow fibre membrane cartridge containing hollow fibres manufactured from semipermeable membranes, which are impermeable to macromolecules but allow the passage of small molecules, the ratio of the number of these hollow fibres to the effective length of the hollow fibres not exceeding a value of 0.5 mm$^{-1}$, and the internal diameter of a hollow fibre not exceeding a value of 0.25 mm.

When compared to the hollow fibre membrane cartridges of an artificial kidney, the hollow fibres of the hollow fibre membrane cartridge according to the invention are remarkably longer, and its number significantly lower. As a consequence, the macromolecules separated by means of liquid chromatography are not mixed in a detrimental manner, when distributed among the various hollow fibres of the hollow fibre membrane cartridge. The specified upper limit for the internal diameter of the individual hollow fibres avoids the separated macromolecules being mixed while flowing through the individual hollow fibres.

The apparatus according to the invention has the advantage, that the concentration and/or the buffer exchange occurs simultaneously with the chromatography, in fact for the whole eluate virtually on-line and in only one step.

Furthermore, it is an object of the invention to develop a method for recovery and buffer exchange and/or concentration of dissolved macromolecules from a mixture of molecules using the apparatus illustrated before, wherein the extraction and/or the exchange of the buffer solution takes place continuously, as the eluate of the liquid chromatography unit flows through the hollow fibres of the hollow fibre membrane cartridge and these hollow fibers are surrounded by counterflowing low-molecular substances dissolved in a solvent.

The method according to the invention has the advantage, that the concentration and/or the buffer exchange takes place immediately, directly following the sequential separation in the liquid chromatography unit and in a continuous manner in only one step, i.e. a countercurrent dialysis for the whole eluate. In this way, the method for concentration and/or buffer exchange is made considerably faster and can take place in only one unit, namely in a hollow fibre membrane suitable for countercurrent dialysis. Thus, when the method according to the invention is applied, the outlay of equipment needed is considerably reduced.

In a particularly advantageous development of the method according to the invention, the solvent counterflowing with respect to the eluate contains specific low-molecular substrates for enzymatic detection. In this way, information about the macromolecular species contained in the sequentially flowing eluate becomes available in only one step of the process. In this kind of enzymatic detection, the macromolecular substances to be tested do not undergo any reaction and they are recovered unmodified in the preparation.

BRIEF DESCRIPTION OF THE DRAWING

In sole FIGURE shows a liquid chromatography unit in conjunction with a hollow fiber membrane cartridge.

DESCRIPTION OF THE PREFERRED EMBODIMENTS

Three embodiments of the invention will be illustrated below by means of a drawing showing schematically the structure of a liquid chromatography unit in conjunction with a hollow fibre membrane cartridge.

The liquid chromatography column as whole is indicated in the drawing by reference number 1. The liquid chromatography unit 1 shows on its top an inlet 2 and in its bottom part an outlet 3. The mixture of macromolecular substances to be separated, e.g. a body fluid containing a suitable buffer solution is added through the inlet 2. The macromolecular species present in the mixture flowing through the liquid chromatography unit 1 are sequentially displaced in a known manner, and at the same time, eventually diluted and/or mixed with low-molecular substances. The various macromolecular species leave the column through the outlet 3 in a displaced manner, i.e. sequentially. However, the eluate leaving through outlet 3 contains the buffer solutions added before or during the separation; these buffer solutions are undesired in or even detrimental for the preparation recovered.

In order to withdraw or to exchange the undesired or detrimental substances of the buffer solution, a hollow fibre membrane cartridge 4 is connected to the outlet 3 of the liquid chromatography unit 1; by means of this cartridge withdrawal and/or exchange of buffer solutions is carried out applying countercurrent dialysis.

This hollow fibre membrane cartridge contains a certain number of semipermeable hollow fibres 5, i.e. they allow the passage of low-molecular substances while retaining macromolecular substances. The eluate of the liquid chromatography unit 1 flows through the internal bore of the hollow fibres 5, in the direction indicated by arrow 6. At the same time, the hollow fibres 5 are surrounded all along by dialysis fluid flowing in the opposite direction to the arrows 6. The buffer solution in the eluate can be influenced (i.e. withdrawn or exchanged) by changing the composition of the dialysis fluid. The dialysis fluid may also contain, if necessary, specific low-molecular substrates for enzymatic detection.

In order to obtain sufficient enough contact between the eluate flowing through the hollow fibres 5 and the dialysis fluid counterflowing, without revoking the separation achieved by liquid chromatography, the hollow fibre membrane cartridge according to the invention was designed with a ratio of the number of hollow fibres 5 to the effective length of the hollow fibres less than 0.5 mm$^{-1}$ as well as with an internal diameter of the hollow fibres of less than 0.25 mm.

The dialysis fluid is added to the hollow fibre membrane cartridge through the connections 7 and 8. The direction of flow is shown by the arrows 9.

All connections of the hollow fibre membrane cartridge 4 can be designed as plug or screw connections being quickly removable. This allows to exchange the cartridge 4 quickly and, if necessary, to connect several cartridges 4 to each other in a suitable manner.

The method according to the invention will be illustrated below by means of three practical examples, the first of which relates to the concentration of the buffer solution containing the macromolecules, the second to the buffer exchange and the third to an additional enzymatic detection:

EXAMPLE 1

A mixture of biological macromolecules, e.g. a cell crude extract, is chromatographically separated by gel filtration, e.g. with Sephacryl S-200 HR. The unavoidable dilution of the sample solution, which is coupled to the separation principle, is reverted by concentration using a hollow fibre membrane cartridge. A hygroscopic solution of 20% polyethylen glycol (MW=20.000) in water is used in counterflow. In this way, the buffer solution is withdrawn from the eluate through the semipermeable membrane, and the macromolecule solution is concentrated.

EXAMPLE 2

A mixture of biological macromolecules, e.g. blood plasma, is separated by means of covalent chromatography, e.g. with Thiol-Sepharose. Substances needed for the separation, e.g. β-mercaptoethanol and 2-thiopyridyl groups, which would make a subsequent optical detection unfeasible, can be removed by means of a hollow fibre membrane cartridge connected to the chromatography unit. In this case, a physiological sodium chloride solution is used in counterflow.

EXAMPLE 3

The experiments specified in the examples 1 or 2 are modified, as a second hollow fibre membrane cartridge is serially connected to the first one. For example, NADH and pyruvate can be introduced in the buffer solution by dialysis. For detection of the enzyme lactate dehydrogenase, the loss of NADH after passage through the cartridge, which is due to the enzymatic conversion of pyruvate to lactate by the lactate dehydrogenase, can be photometrically monitored (e.g. at 340 nm).

We claim:

1. An apparatus for recovery and buffer exchange and/or concentration of dissolved macromolecules from a mixture of macromolecules, comprising a liquid chromatography unit and at least one hollow fibre membrane cartridge provided in the outlet tubing of the liquid chromatography unit, characterised in that the hollow fibre membrane cartridge contains hollow fibres manufactured from semipermeable membranes, which are impermeable to macromolecules but allow the passage of small molecules, and in that the ratio of the number of these hollow fibres to the effective length of the hollow fibres does not exceed a value of 0.5 $mm^{-1}$ and that the internal diameter of a hollow fibre does not exceed a value of 0.25 mm.

2. A method of recovery and buffer exchange and/or concentration of dissolved macromolecules from a mixture of macromolecules using an apparatus according to claim 1, characterised in that the extraction and/or the exchange of the buffer solution takes place continuously, as the eluate from the liquid chromatography unit flows through the hollow fibres of the hollow fibre membrane cartridge and these hollow fibres are surrounded by counterflowing low-molecular substances dissolved in a solvent.

3. A method according to claim 2, characterised in that the solvent counterflowing with respect to the eluate contains specific low-molecular substrates for enzymatic detection.

* * * * *